United States Patent [19]

D'Alelio

[11] 4,052,416
[45] Oct. 4, 1977

[54] HALOGENATED ESTERS OF PHOSPHORUS-CONTAINING ACIDS (III)

[76] Inventor: Gaetano F. D'Alelio, 2011 E. Cedar St., South Bend, Ind. 46617

[21] Appl. No.: 646,504

[22] Filed: Jan. 5, 1976

Related U.S. Application Data

[63] Continuation-in-part of Ser. No. 539,812, Jan. 9, 1975, Pat. No. 3,970,727, which is a continuation-in-part of Ser. No. 179,543, Sept. 10, 1971, Pat. No. 3,780,144, which is a continuation of Ser. No. 785,335, Dec. 19, 1968, abandoned.

[51] Int. Cl.$^2$ .............................................. C07F 9/40
[52] U.S. Cl. .............................................. 260/348.42
[58] Field of Search .................................. 260/348 R

[56] References Cited

U.S. PATENT DOCUMENTS

| | | | |
|---|---|---|---|
| 2,770,610 | 11/1956 | Hardy et al. | 260/348 R |
| 2,938,877 | 5/1960 | Mack et al. | 260/23 |
| 3,042,701 | 7/1962 | Birum | 260/461 |
| 3,213,057 | 10/1965 | Ritt et al. | 260/47 |
| 3,485,897 | 12/1969 | Jenkner | 260/932 |

Primary Examiner—Norma S. Milestone
Attorney, Agent, or Firm—Walter J. Monacelli

[57] ABSTRACT

This invention deals with new phosphorus-containing esters having the formula

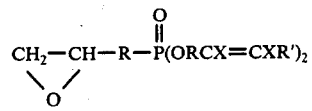

wherein
R represents a divalent hydrocarbon radical containing 1-20 carbon atoms;
R' represents X, hydrogen or R";
R" represents a monovalent hydrocarbon radical containing 1-20 carbon atoms; and
X represents chlorine or bromine.

These new esters are useful particularly as fire retardants, agricultural chemicals, fuel additives, plasticizers, monomers and intermediates for the synthesis of other useful derivatives.

4 Claims, No Drawings

HALOGENATED ESTERS OF PHOSPHORUS-CONTAINING ACIDS (III)

This application is a continuation-in-part of co-pending application Ser. No. 539,812, filed Jan. 9, 1975, now U.S. Pat. No. 3,970,727, which in turn is a continuation-in-part of co-pending application Ser. No. 179,543, filed Sept. 10, 1971, issued as U.S. Pat. No. 3,780,144 on Dec. 18, 1975, which in turn is a continuation of application Ser. No. 785,335, filed Dec. 19, 1968, now abandoned.

BACKGROUND OF THE INVENTION

1. Field of the Invention

This invention involves new esters containing both phosphorus and halogen atoms in their structures. More specifically, it concerns the phosphonium esters of halogenated acetylenic alcohols.

2. Related Prior Art

No pertinent prior art is known.

STATEMENT OF THE INVENTION

The esters of this invention are represented by the formula:

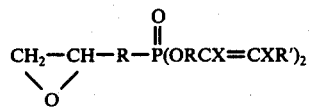

wherein
R represents a divalent hydrocarbon radical containing 1–20 carbon atoms;
R' represents X, hydrogen or R";
R" represents a monovalent hydrocarbon radical containing 1–20 carbon atoms; and
X represents chlorine or bromine.

The esters of this invention are prepared readily by the following reaction using one mole of phosphate reagent per mole of oxirane to be reacted:

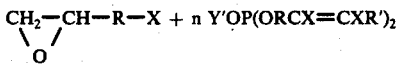

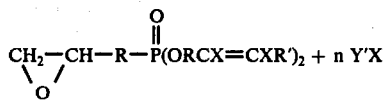

wherein Y' represents H or $-RCX=CXR'$ with the by-product Y'X representing HX or $XRCX-CXR'$ both of which may be distilled from the reaction mass leaving the desired products as the residue. The carbon atom of the R group in the oxirane molecule to which the X is attached is advantageously an aliphatic carbon atom to facilitate the reaction.

This reaction may be activated by the presence of a small amount of peroxy compound such as benzoyl peroxide. However this may not be desirable when an easily polymerizable compound is being prepared in which case the activation may be effected thermally and advantageously in the presence of a polymerization inhibitor such as t-butyl catechol.

The divalent hydrocarbon radical represented by R in the above formulas can be aliphatic, cycloaliphatic or aromatic and can be saturated or have ethylenic or acetylenic unsaturation therein. Aliphatic radicals include aryl-substituted aliphatic radicals such as phenylethylene, phenylenedimethylene, etc.; aromatic radicals include alkyl, alkenyl and alkynyl substituted aromatic radicals such as tolylene, xylylene, ethylphenylene, vinylphenylene, propargylphenylene, etc.; and cycloaliphatic radicals include alkyl, alkenyl, alkynyl and aryl substituted cycloaliphatic radicals such as ethylcyclohexylene, vinylcyclohexylene, propargylcyclohexylene, phenylcycloheptylene, tolylcyclopentylene, etc. The simpler and smaller of these radicals are preferred for obvious reasons, but the more complicated radicals can also be used and are included in the scope of this invention. In the R group attached to the oxirane radical, the carbon atom to which the phosphorus is attached is advantageously an aliphatic carbon, preferably in a $CH_2$ group, so that the halide from which it is formed is more easily reacted in the preparation of the compounds of this invention.

These divalent hydrocarbon radicals are illustrated by the following typical radicals: $-CH_2-$; $-(CH_2)_2-$; $-(CH_2)_7-$; $-(CH_2)_{12}-$; $-C(CH_3)_2-$; $-CH(CH_3)-$; $-CH(C_6H_5)-$; $-CH(C_6H_{11})-$; $-CH(C_4H_9)-$; $-CH(C_8H_{17})-$; $-CH_3CH(C_6H_5CH_3)-$; $-CH(CH_3)CH_2CH_2-$; $-CH_2CH=CHCH_2-$; $-CH_2C\equiv CCH_2-$; $-CH_2CH(CH=CH_2)-$; $-CH(C\equiv CH)CH_2-$; $-CH(CH_2C_6H_5)CH_2-$; $-CH_2C_6H_4CH_2-$; $-CH_2CH_2C_6H_4-$; $-C_6H_4-$; $-C_6H_3(CH_3)-$; $-C_{10}H_6-$; $-C_{10}H_5(C_2H_5)-$; $-C_6H_3(CH=CH_2)-$; $-C_6H_{10}-$; $-C_5H_8-$; $-C_7H_{12}-$; $-C_6H_9(CH_3)-$; $-C_6H_9(C_6H_5)-$; $-C_7H_{11}(CH_2C\equiv CH)-$; $-CH_2C_6H_{10}CH_2-$; $-CH_2CH_2C_6H_{10}-$; $-(CH_2)_8CH=CH(CH_2)_{10}-$; and the like.

The organic moiety

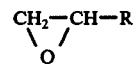

is the residue from the compound

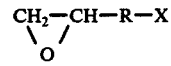

which may be used in the preparation of the compounds of this invention. Compounds which may be used in such preparations and which illustrate the oxirane-containing moieties include the following:

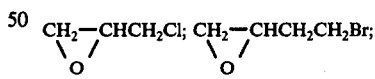

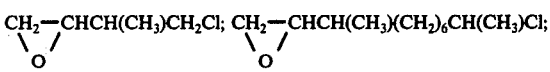

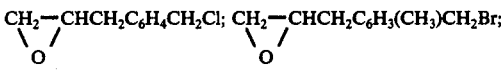

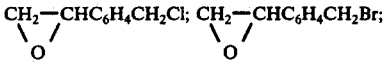

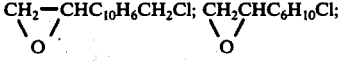

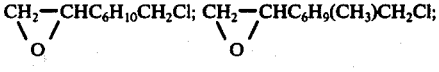

-continued

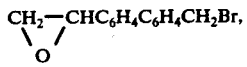

and the like.

The above reaction for the preparation of the compounds of this invention is advantageously conducted in the temperature range of 0° to 100° C., and preferably, especially when groups are present having a strong tendency to polymerize, in the presence of a polymerization inhibitor of the various well known types, such as t-butyl catechol. When polymerization inhibitor is omitted the product may be at least partially polymerized. Preferably a polymerization inhibitor is used during the preparation of the ester so that where polymerizable groups are present which have a strong tendency to polymerize polymerization may be conducted subsequently either by itself or with copolymerizable alkylene oxide compounds such as ethylene oxide, propylene oxide, glycidyl acrylate, etc., or the monomer may be used for various other purposes as indicated herein.

The period required to complete reaction varies according to the temperature used. For example, at 100° C a substantial amount of reaction is effected within 10 minutes, whereas at least 30 minutes, preferably at least one hour, is desired to effect substantial reaction at 0° C. In most cases a period of 1-5 hours is used to insure complete reaction.

Instead of using the halogenated acetylenic alcohols with the phosphorus halides as shown in the above reaction, the acetylenic alcohol may be converted first to the ester and the acetylenic ester posthalogenated to the desired product. Ester exchange reactions can also be used to prepare the esters of this invention.

The (—ORCX=CXR') type of esters of this invention differ from the esters of halogenated saturated alcohols, for example (—OCH$_2$CHXCH$_2$X), having much greater hydrolytic stability of the halogen atoms than the latter type of esters which show a much greater tendency to lose halogen. This loss of halogen occurs under conditions of high humidity, thereby limiting the utility of the saturated compound.

The novel phosphorus-containing esters of this invention are self-extinguishing when ignited and thus are particularly useful as fire-retardant additives for a host of other materials and compounds, particularly those of a resinous or polymeric nature, for example, when added to polymethyl methacrylate, polystryene, cellulose acetate, cellulose butyrate, the polyesters, the polyurethanes, rubbers, nylon and others. They can also be used as fire-retardant impregnants for porous bodies, such as paper, wood, fiberboard, cork, etc.

As organic compounds containing phosphorus and halogen atoms they are useful also as agricultural chemicals in the fields of insecticides, herbicides, pesticides, etc., as well as gasoline additives to function as metal scavengers for anti-knock gasoline containing organolead, -boron or metallo-organo-compounds. Particularly are they useful as chemical intermediates in the synthesis of a host of other useful derivatives. The halo compounds can be halogenated further at the ethylenic double bond to produce higher halogenated compounds which have even greater self-extinguishing properties then the dihalo compounds. They also add to olefinic double bonds of the unsaturated compounds to yield plasticizers as well as polymerizable monomers. The epoxy groups can also be converted to glycols which can be used as modifers of urethane polymers, polyesters, cellulose, etc.

When the oxirane or epoxy group is converted to the corresponding glycol, these compounds can be used as modifiers in polymerization reactions or can be reacted with other functional molecules such as with the isocyanates, acid anhydrides, acid chlorides, oxirane compounds, etc., or when they also contain an unsaturated olefinic group they can be homopolymerized or copolymerized with other monomers; or when they contain an amide group they can be reacted with aldehydes and polymerized alone or copolymerized with urea or melamine, or their methylol compounds can be reacted with cellulose or wool, etc.

Derivatives prepared from the compounds of this invention also find utility as flame-retardant additives and impregnants, as agricultural chemicals and as fuel additives. In addition, when the parent compounds or derivatives contain functional groups, such as the OH groups, they can be used as modifiers in polymerization reactions or can be reacted with other functional molecules such as with the isocyanates, acid anhydrides, acid chlorides, oxirane compounds, etc., or when they contain an unsaturated olefinic group they can be homopolymerized or copolymerized with other monomers; or when they contain an amide group they can be reacted with aldehydes and polymerized alone or copolymerized with urea or melamine, or their methylol compounds can be reacted with cellulose or wool, etc.

The practice of this invention is illustrated by the following examples. These examples are given merely by way of illustration and are not intended to limit the scope of the invention in any way nor the manner in which the invention can be practiced. Unless specifically indicated otherwise, parts and percentages are given as parts and percentages by weight.

EXAMPLE I

One hundred forty-five parts of 1,2,3-trichloropropane are added to a solution of 106 parts of sodium carbonate dissolved in 900 parts of water and the mixtue refluxed for ten hours. The water layer is then separated from the oily layer which is dried over anhydrous sodium carbonate, separated by filtration and distilled. There is obtained 115 parts of 2,3-dichloro-2-propene-l-ol, ClCH=CClCH$_2$OH, (I), b.p. 45°–46° C./1.5 mm; yield 91%.

EXAMPLE II (a) To 250 parts of carbon tetrachloride is added 56 parts of propargyl alcohol (A) and to this solution there is added slowly, at room temperature, a solution of 160 parts of bromine in 250 parts of carbon tetrachloride and allowed to react at room temperature for two hours. Then the mixture is heated to 30°–40° C. for two hours. The product is distilled to recover the carbon tetrachloride and the 2,3-dibromo-2-propene-l-ol, BrCH=CBrCH$_2$OH, (II), b.p. 51°–52° C./0.7 mm; yield 93%. (b) Treatment of 1,2,3-tribromopropene with aqueous sodium carbonate by the procedure of Example I yields the same 2,3-dibromo-2-propene-l-ol.

EXAMPLE III

The reaction of 2-methyl-3-butyn-2-ol (B) with NaOCl under an inert atmosphere of nitrogen according to the procedure given in the Bull. soc. chim. (France), p. 1615 (1965) gives an 87% yield of 4-chloro-2-methyl-3-butyl-2-ol,

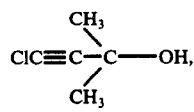 (III)

b.p. 54°-56° C./18 mm. This may be halogenated by the process of Example II to give the trihalo acetylenic alcohol $Cl(Br)C=C(Br)C(CH_3)_2OH$ or by similarly chlorinating to give $Cl_2C=C(Cl)C(CH_3)_2OH$.

EXAMPLE IV

The reaction of 2-methyl-3-butyl-2-ol in water with $Br_2$ and NaOH by the procedure given in Ann. Chem. (Rome), 47, 118 (1957) yield 4-bromo-2-methyl-3-butyn-2-ol,

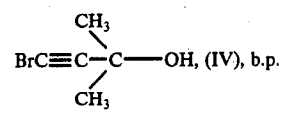 (IV), b.p.

92°-93° C./22 mm. This may be halogenated by the process of Example II to give the trihalo acetylenic alcohol $Br_2C=C(Br)C(CH_3)_2OH$.

EXAMPLE V

The procedure of Example II(a) is repeated using instead of propargyl alcohol, one equivalent wieight of the following acetylenic alcohols to obtain the halo-derivative corresponding to the alcohol used:

| Acetylenic Alcohol | | Dibromoethylene Derivative | |
|---|---|---|---|
| $HC{\equiv}C-CH(CH_3)-OH$ | (C) | $HC(Br)=C(Br)-CH(CH_3)-OH$ | (V) |
| $HC{\equiv}C-CH(C_2H_5)-OH$ | (D) | $HC(Br)=C(Br)-CH(C_2H_5)-OH$ | (VI) |
| $HC{\equiv}C-CH(C_3H_7)-OH$ | (E) | $HC(Br)=C(Br)-CH(C_3H_7)-OH$ | (VII) |
| $HC{\equiv}C-CH(C_4H_9)-OH$ | (F) | $HC(Br)=C(Br)-CH(C_4H_9)-OH$ | (VIII) |
| $HC{\equiv}C-CH(C_8H_{17})-OH$ | (G) | $HC(Br)=C(Br)-CH(C_8H_{17})-OH$ | (IX) |
| $HC{\equiv}C-CH(C_6H_5)-OH$ | (H) | $HC(Br)=C(Br)-CH(C_6H_5)-OH$ | (X) |
| $HC{\equiv}C-C(CH_3)_2-OH$ | (B) | $HC(Br)=C(Br)-C(CH_3)_2-OH$ | (XI) |
| $HC{\equiv}C-C(CH_3)(C_2H_5)-OH$ | (I) | $HC(Br)=C(Br)-C(CH_3)(C_2H_5)-OH$ | (XII) |
| $HC{\equiv}C-C(CH_3)(C_4H_9)-OH$ | (J) | $HC(Br)=C(Br)-C(CH_3)(C_4H_9)-OH$ | (XIII) |
| $HC{\equiv}C-C(C_4H_9)_2-OH$ | (K) | $HC(Br)=C(Br)-C(C_4H_9)_2-OH$ | (XIV) |
| $H_3C-C{\equiv}C-CH_2OH$ | (L) | $CH_3C(Br)=C(Br)-CH_2OH$ | (XV) |
| $H_3C-C{\equiv}C-CH_2CH_2OH$ | (M) | $CH_3C(Br)=C(Br)-CH_2CH_2OH$ | (XVI) |
| $C_6H_5C{\equiv}C-(CH_2)_{10}OH$ | (N) | $C_6H_5C(Br)=C(Br)-(CH_2)_{10}OH$ | (XVII) |
| $H_{41}C_{20}C{\equiv}C-CH_2OH$ | (O) | $H_{41}C_{20}C(Br)=C(Br)-CH_2OH$ | (XVIII) |

-continued

| Acetylenic Alcohol | | Dibromoethylene Derivative | |
|---|---|---|---|
| H₃CC≡C—CH₂CH(CH₃)—OH | (P) | H₃CC(Br)=C(Br)—CH₂CH(CH₃)—OH | (XIX) |
| C₄H₉C≡C—CH₂OH | (Q) | H₉C₄C(Br)=C(Br)—CH₂OH | (XX) |
| C₆H₅C≡C—CH₂OH | (R) | C₆H₅C(Br)=C(Br)—CH₂OH | (XXI) |
| C₆H₅C≡C—CH₂CH₂OH | (S) | C₆H₅C(Br)=C(Br)—CH₂CH₂OH | (XXII) |
| C₆H₁₁C≡C—CH₂OH | (T) | C₆H₁₁C(Br)=C(Br)—CH₂OH | (XXIII) |
| C₆H₅C≡C—CH(CH₃)—OH | (U) | C₆H₅C(Br)=C(Br)—CH(CH₃)—OH | (XXIV) |
| C₆H₅C≡C—C(CH₃)₂—OH | (V) | C₆H₅C(Br)=C(Br)—C(CH₃)₂—OH | (XXV) |
| ClC≡C—C(CH₃)₂—OH | (III) | ClC(Br)=C(Br)—C(CH₃)₂—OH | (XXVI) |
| BrC≡C—C(CH₃)₂—OH | (IV) | BrC(Br)=C(Br)—C(CH₃)₂—OH | (XXVII) |
| C₁₀H₇C≡CCH₂OH | (W) | C₁₀H₇C(Br)=C(Br)—CH₂OH | (XXVIII) |

EXAMPLE VI a. In a solution of 56 parts of propargyl alcohol and 0.1 part of iodine in 300 parts of tetrachloroethylene is slowly passed chlorine gas while exposed to an ultraviolet lamp until 70 parts of chlorine are reacted. The halogenated product is then recovered by distillation and the majority of the product is identical to the 2,3-dichloro-2-propene-1-ol of Example I.

b. In a similar manner there is prepared

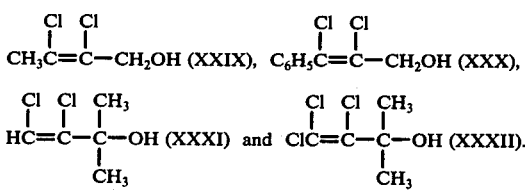

CH₃C(Cl)=C(Cl)—CH₂OH (XXIX), C₆H₅C(Cl)=C(Cl)—CH₂OH (XXX),

HC=C(Cl)—C(Cl)(CH₃)—C(CH₃)—OH (XXXI) and ClC=C(Cl)—C(CH₃)₂—OH (XXXII).

The halogenated acetylenic alcohols prepared in the above examples may be used in preparing the P(ORCX=CXR')₃ and HOP(ORCX=CXR')₂ reagents used for preparing the new compositions of this invention as illustrated in some of the following examples.

EXAMPLE VII a. The phosphite ester,

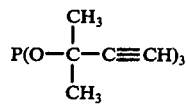

is prepared from PCl₃ and

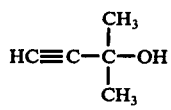

(B) by the procedure given in U.S. Patent 2,278,791, December 27, 1955, and converted by the procedure of Example II(a) by reaction with Br₂ to

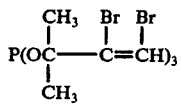

b. In a manner similar to the procedure of VII(a) the acetylenic alcohols III, IV, C, D, L and M are converted to the phosphite esters, P(ORC≡CR")₃, and by post bromination to esters corresponding to the formula

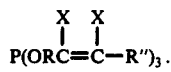

EXAMPLE VIII

A mixture of 46 parts of PCl$_3$, 126 parts of 2,3-dichloro-2-propene-1-ol and 150 parts of toluene is refluxed until no more HCl is evolved from the reaction. The mixture is then allowed to cool to room temperature; then 5 parts of anhydrous sodium carbonate and 3 parts of decolorizing carbon are added to the solution and allowed to stand with stirring for 8 to 24 hours. The solution is then filtered and the filtrate distilled at 0.5 to 14 mm Hg pressure to recover the toluene. The yield of almost colorless residue is 96% of the theoretical amount. The infrared spectra of the product confirms the absence of the band for the -OH group of the alcohol and the presence of the band for the ester group. The product is a viscous oil insoluble in water but soluble in benzene and toluene. The elemental analysis of the product: percent C, 26.95; percent H, 2.24; percent Cl, 52.56; are in close agreement with the theoretical values of C, 26.42; H, 2.20; Cl, 52.02 for P(OCH$_2$CCl=CHCl)$_3$.

The boiling point of the product is higher than 120° C. at 0.5 mm Hg. Attempts to distill the product at higher pressure results in secondary reactions which change the nature of the product, which product, however, is still self-extinguishing. Other triesters of this type having other R groups in place of the —CH$_2$— and/or having bromine in place of the chlorine or having the tetrachloro or tetrabromo structure can be similarly prepared for use as intermediates in preparing phosphate esters of the present invention.

EXAMPLE IX

A mixture of 10.15 parts of P(OCH$_2$CCl=CHCl)$_3$ and 15 parts of CH$_3$COOH are heated at 100° C. for two hours following which it is distilled at 15 mm pressure to recover 42 parts of CH$_3$COOCH$_2$CCl=CHCl, leaving as a residue 86.2 parts of HOP(OCH$_2$CCl=CHCl)$_2$ which on analysis is shown to contain 46.4% of Cl compared to a theoretical value of 47.3.

Various other di and trihalogenated acetylenic alcohols can be used to prepare various HOP-(ORCX=CXR')$_2$ reagents suitable for use in the practice of this invention.

EXAMPLE X

A mixture of 40.6 parts of P(OCH$_2$CCl=CHCl)$_3$ and 8.2 parts of P(OH)$_3$ are heated at 75° C. for three hours and there is obtained the viscous product comprising as the major product 48.8 parts of HOP-(OCH$_2$CCl=CHCl)$_2$.

By substituting various other P(ORCX=CXR')$_3$ compounds for the P(OCH$_2$CCl=CHCl)$_3$, other HOP-(ORCX=CXR')$_2$ reagents useful in the practice of this invention may be prepared.

EXAMPLE XI (a) To 47.8 parts of HOP(OCH$_2$CBr=CHBr)$_2$ in 150 parts of toluene under a nitrogen atmosphere, there is added slowly at 20°-30° C. a solution containing 100 parts of toluene, 9.3 parts of

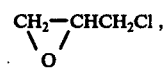

0.5 parts of tertiary butyl catechol and 5.9 parts of trimethyl amine, and the mixture stirred for 3 hours. The precipitated amine hydrochloride (CH$_3$)$_3$N.HCl is removed by filtration, and the filtrate containing the product

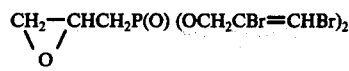

is washed with distilled water until the washings are neutral. The toluene solution containing the monomer,

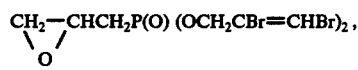

can be used as prepared for the preparation of polymers and copolymers, or grafted to cellulose fibers, or the toluene can be removed by distillation at reduced pressures leaving an almost quantitative yield of the monomer whose structure is verified by C, H, P, Cl and O analyses.

The procedure of (a) is repeated a number of times using equivalent amounts of the reagents and obtaining the products indicated in the table below.

| | Reagents | Product |
|---|---|---|
| (b) | HOP(OCH$_2$CCl=CHCl)$_2$ + CH$_2$—CHCH$_2$Cl \\O/ | CH$_2$—CHCH$_2$P(O)— \\O/ (OCH$_2$CCl=CHCl)$_2$ |
| (c) | HOP(OCH$_2$CCl=CHCl)$_2$ + CH$_2$—CHCH$_2$CH$_2$Cl \\O/ | CH$_2$—CHCH$_2$P(O)— \\O/ (OCH$_2$CCl=CHCl)$_2$ |
| (d) | HOP(OCH$_2$CCl=CHCl)$_2$ + CH$_2$—CHCH$_2$CH$_2$Br \\O/ | CH$_2$—CH—CH$_2$CH$_2$P(O)— \\O/ (OCH$_2$CCl=CHCl)$_2$ |

-continued

| | Reagents | Product |
|---|---|---|
| (e) | HOP[O(CH$_2$)$_3$CCl=CHCl]$_2$ | CH$_2$—CHCH(CH$_3$)CH$_2$P(O)— \ O /  [O(CH$_2$)$_3$CCl=CHCl]$_2$ |
| | + CH$_2$—CHCH(CH$_3$)CH$_2$Cl \ O / | |
| (f) | HOP(OCH$_2$CCl=CCl$_2$)$_2$ | CH$_2$—CH—CH$_2$C$_6$H$_4$CH$_2$P(O)— \ O /  (OCH$_2$CCl=CCl$_2$)$_2$ |
| | + CH$_2$—CHCH$_2$C$_6$H$_4$CH$_2$Br \ O / | |
| (g) | HOP(OC$_6$H$_4$CCl=CHCl)$_2$ | CH$_2$—CHC$_6$H$_{10}$CH$_2$P(O)— \ O /  (OC$_6$H$_4$CCl=CHCl)$_2$ |
| | + CH$_2$—CHC$_6$H$_{10}$CH$_2$Cl \ O / | |
| (h) | HOP(OCH$_2$CBr=CBr$_2$)$_2$ | CH$_2$—CH(CH$_2$)$_8$P(O)— \ O /  (OCH$_2$CBr=CBr$_2$)$_2$ |
| | + CH$_2$—CH(CH$_2$)$_8$Cl \ O / | |
| (i) | HOP(OCH$_2$CCl=CHCl)$_2$ | CH$_2$—CHC$_6$H$_{10}$CH$_2$P(O)— \ O /  (OCH$_2$CCl=CHCl)$_2$ |
| | + CH$_2$—CHC$_6$H$_{10}$CH$_2$Cl \ O / | |
| (j) | HOP(OCH$_2$CBr=CHBr)$_2$ | CH$_2$—CHC$_6$H$_3$(CH$_3$)CH$_2$P(O)— \ O /  (OCH$_2$CBr=CHBr)$_2$ |
| | + CH$_2$—CHC$_6$H$_3$(CH$_3$)CH$_2$Cl \ O / | |
| (k) | HOP(OCH$_2$CCl=CHCl)$_2$ | CH$_2$—CHC$_{10}$H$_6$CH$_2$P(O)— \ O /  (OCH$_2$CCl=CHCl)$_2$ |
| | + CH$_2$—CHC$_{10}$H$_6$CH$_2$Cl \ O / | |

EXAMPLE XII a. The procedure of Example XI(a) is repeated using equivalent amounts of CH$_2$—CHCH$_2$Cl
\ O / and HOP(OCH$_2$CCl=CCl$_2$)$_2$ to give the ester having the formula

CH$_2$—CHCH$_2$P(O) (OCH$_2$CCl=CCl$_2$)$_2$
\ O / b. The procedure of Example XI(a) is repeated using equivalent amounts of

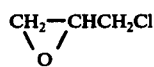

and HOP(OCH$_2$CBr=CBr$_2$)$_2$ to give the ester having the formula

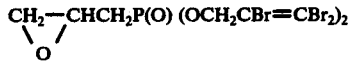

c. The procedure of Example XI(a) is repeated using equivalent amounts of

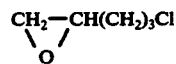

and HOP(OCH$_2$C$_6$H$_4$CCl=C(CH$_3$)Br)$_2$ to give the ester having the formula

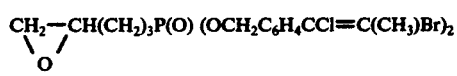

d. The procedure of Example XI(a) is repeated using equivalent amounts of

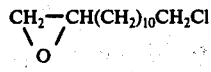

and HOP(OCH$_2$CBr-C(C$_6$H$_5$)Br)$_2$ to give the ester having the formula

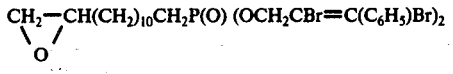

e. The procedure of Example XI(a) is repeated using equivalent amounts of

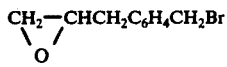

and HOP(OCH$_2$C$_6$H$_4$CCl=CCl$_2$)$_2$ to give the ester having the formula

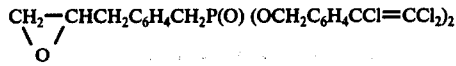

f. The procedure of Example XI(a) is repeated using equivalent amounts of

to give the ester having the formula

g. The procedure of Example XI(a) is repeated using equivalent amounts of

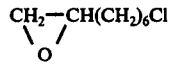

and HOP(OCH$_2$CCl=C(C$_3$H$_7$)Cl)$_2$ to give the ester having the formula

h. The procedure of Example (XI(a) is repeated using equivalent amounts of

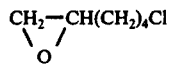

and HOP(OCH$_2$CCl=C(C$_8$H$_{16}$)Cl)$_2$ to give the ester having the formula

EXAMPLE XIII

Samples of the various phosphorus esters of Examples XI–XII are placed individually in a microcrucible and in each case the contents ignited by the flame of a microburner. When the flame is withdrawn, in each case burning stops completely.

EXAMPLE XIV a. An equimolar mixture of P(OCH$_2$CCL=CHCl)$_3$ and

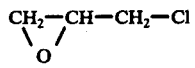

is heated at 100° C for 3 hours in the presence of 0.5% t-butyl catechol following which the mixture is distilled to remove ClCH=CClCH$_2$Cl leaving as a residue the ester

The above product is verified by C, H, P, Cl and O analyses.

EXAMPLE XV

A mixture of 50 parts of ethylene oxide, 5 parts of

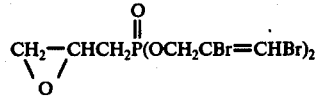

and 0.5 parts of sodium hydroxide is polymerized in a sealed container under nitrogen at 80° C until a hard polymer is obtained, which is self-extinguishing. This polymer has a mixture of repeating units of the formulas

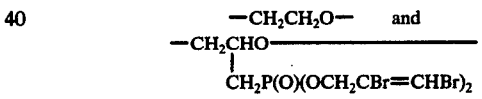

Similar self-extinguishing polymers are obtained when, instead of

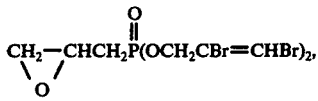

the individual esters of Examples XI–XII are used.

EXAMPLE XVI

The procedure of Example XV is repeated using instead of ethylene oxide the monomers propylene oxide, butylene oxide and styrene oxide, respectively, and self-extinguishing polymers are obtained in each case.

EXAMPLE XVII

Ten parts of

are added respectively to each of the following, which are approximately 50% solvent and 50% solids: (a) a clear alkyd varnish, (b) a cellulose acetate-butyrate lacquer, (c) a white-pigment oil-modified epoxy paint, and (d) a pigmented urethane-type paint; then films are cast from the mixtures and allowed to dry or cure for four days. Attempts to ignite the resulting films showed in each case that they are self-extinguishing. Similar results are obtained when the other esters selected from Examples XI–XII are similarly tested.

As shown above the phosphorus-containing esters of this invention having oxirane groups therein are polymerizable by themselves or in mixtures with other oxirane monomers.

In producing self-extinguishing copolymers with such copolymerizing monomers, such properties are exhibited with as little as 0.1 percent by weight, preferably at least 1 percent by weight, of a monomer of this invention. In blends of homopolymers or copolymers of these phosphorus-containing esters with other polymers, there is advantageously at least 0.1 percent, preferably at least 1 percent by weight, of the product represented by the phosphorus-containing ester portion.

While certain features of the invention have been described in detail with respect to the various embodiments thereof, it will, of course, be apparent that other modifications may be made within the spirit and scope of this invention, and it is not intended to limit the invention to the exact details shown above except insofar as they are defined in the following claims:

The invention claimed is:

1. A phosphorus halogen-containing compound having the formula

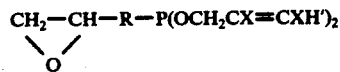

wherein X represents Cl or Br and R represents $CH_2$ or $CH_2CH_2$.

2. The compound of claim 1 having the formula

3. The compound of claim 1 having the formula

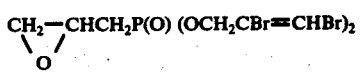

4. The compound of claim 1 having the formula

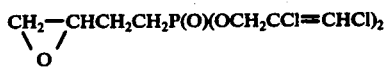

* * * * *

UNITED STATES PATENT OFFICE
CERTIFICATE OF CORRECTION

Patent No. 4,052,416           Dated October 4, 1977

Inventor(s) Gaetano F. D'Alelio

It is certified that error appears in the above-identified patent and that said Letters Patent are hereby corrected as shown below:

Col. 16, lines 6-9, correct the formula to read:

Signed and Sealed this
Seventh Day of March 1978

[SEAL]

Attest:

RUTH C. MASON  
Attesting Officer

LUTRELLE F. PARKER  
Acting Commissioner of Patents and Trademarks